United States Patent
Forman et al.

(10) Patent No.: US 10,717,976 B2
(45) Date of Patent: *Jul. 21, 2020

(54) NUCLEIC ACID PURIFICATION

(71) Applicant: ZYMO RESEARCH CORPORATION, Irvine, CA (US)

(72) Inventors: Stanislav Forman, Newport Beach, CA (US); Xiyu Jia, Newport Beach, CA (US)

(73) Assignee: ZYMO RESEARCH CORPORATION, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/961,652

(22) Filed: Dec. 7, 2015

(65) Prior Publication Data

US 2016/0319271 A1 Nov. 3, 2016
US 2017/0204397 A9 Jul. 20, 2017

Related U.S. Application Data

(63) Continuation of application No. 13/943,986, filed on Jul. 17, 2013, now Pat. No. 9,206,469.

(60) Provisional application No. 61/673,106, filed on Jul. 18, 2012.

(51) Int. Cl.

| | |
|---|---|
| *C12N 1/08* | (2006.01) |
| *C12Q 1/68* | (2018.01) |
| *C12N 15/10* | (2006.01) |
| *C12Q 1/6806* | (2018.01) |
| *A61K 31/70* | (2006.01) |

(52) U.S. Cl.
CPC ..... *C12N 15/1006* (2013.01); *C12N 15/1013* (2013.01); *C12Q 1/6806* (2013.01)

(58) Field of Classification Search
CPC ............ C12N 15/1006; C12N 15/1013; C12Q 1/6806
See application file for complete search history.

(56) References Cited

U.S. PATENT DOCUMENTS

| | | | |
|---|---|---|---|
| 4,843,155 A | | 6/1989 | Chomczynski |
| 5,234,809 A | * | 8/1993 | Boom et al. |
| 5,346,994 A | | 9/1994 | Chomczynski |
| 6,027,945 A | | 2/2000 | Smith et al. |
| 7,329,491 B2 | * | 2/2008 | Kirchgesser et al. |
| 7,794,932 B2 | | 9/2010 | Chomczynski |
| 8,367,817 B2 | | 2/2013 | Chomczynski |
| 9,051,563 B2 | | 6/2015 | Forman |
| 9,206,469 B2 | * | 12/2015 | Forman et al. |
| 2004/0181049 A1 | | 9/2004 | Orr et al. |
| 2005/0123965 A1 | | 6/2005 | Yamashita et al. |
| 2005/0233333 A1 | | 10/2005 | Chomczynski |
| 2008/0026451 A1 | | 1/2008 | Braman et al. |
| 2012/0184725 A1 | | 7/2012 | Forman |
| 2013/0225801 A1 | * | 8/2013 | Christoffel |

FOREIGN PATENT DOCUMENTS

| | | |
|---|---|---|
| CA | 2142910 | 8/2002 |
| EP | 2345719 | 7/2011 |
| EP | 2 479 274 | 7/2012 |
| WO | WO 98/31840 | 7/1998 |
| WO | WO 2005/012523 | 2/2005 |

OTHER PUBLICATIONS

Breadmore et al., "Microchip-based purification of DNA from biological samples", *Analytical Chemistry*, 75(8): 1880-1886, 2003.
Collart and Oliviero, "Preparation of yeast RNA", Current Protocols in Molecular Biology, John Wiley & Sons, 1993. 13.12.1-13.12.5.
Ding et al., "Using silica particles to isolate total RNA from plant tissues recalcitrant to extraction in guanidine thiocyanate," *Anal. Biochem.*, 374:426-428, 2007.
Eriksson and Björkman, "Handling of blood samples for determination of thalidomide", *Clinical Chemistry*, 43(6):1094-1096, 1997.
Monstein et al., "RNA Extraction from gastrointestinal tract and pancreas by modified chomczynski and sacchi method," *Biotechniques*, 19(3):340-344, 1995.
Sharp, D.W.A, ed. "Alcohols." *The Penguin Dictionary of Chemistry*, 2nd ed., 18, 1991.
Tian et al., "Evaluation of silica resins for direct and efficient extinction of DNA from complex biological matrices in a miniatuiized forma", *Analytical Biochemistry*, 283(2):175-191, 2000.
Zumbo, "Phenol-chloroform Extraction" protocol from the laboratory of Christopher E. Mason, Weill Cornell Medical College (http://physiology.med.cornell.edu/faculty/mason/lab/zumbo/files/PHENOL-CHLOROFORM.pdf), posted on Aug. 2, 2012.

* cited by examiner

*Primary Examiner* — Quang Nguyen
(74) *Attorney, Agent, or Firm* — Parker Highlander PLLC

(57) ABSTRACT

Methods and composition for nucleic acid isolation are provided. In one embodiment, a method is provided for nucleic acid purification from biological samples, such as whole blood samples, extracted with phenol-based denaturing solvents, which does not require phase separation or nucleic acid precipitation. Methods according to the invention may also be used for of small RNAs (e.g., siRNAs or miRNAs) purification and are amenable to automation.

18 Claims, 7 Drawing Sheets

US 10,717,976 B2

NUCLEIC ACID PURIFICATION

The present application is a continuation of U.S. patent application Ser. No. 13/943,986, filed Jul. 17, 2013, which claims the priority benefit of U.S. provisional application No. 61/673,106, filed Jul. 18, 2012, which is incorporated herein by reference in its entirety.

This application is also related to U.S. patent application Ser. No. 13/349,020, filed Jan. 12, 2012, now U.S. Pat. No. 9,051,563, and U.S. Provisional Patent Application No. 61/432,749, filed Jan. 14, 2011, each of which is incorporated herein by reference in its entirety.

BACKGROUND

Field of the Invention

The present invention generally relates to biochemistry and molecular biology. More specifically, the invention relates to methods and compositions for purification of nucleic acid molecules.

Description of the Related Art

A variety of protocols have been developed for purification of nucleic acids. One crucial step in many purification protocols involves the separation of nucleic acids from protein and lipid molecules that constitute cells and tissue matrices. Once denatured, proteins are typically highly hydrophobic, while nucleic acids remain hydrophilic. Accordingly, organic solvents, such phenol, have been widely used to solubilize proteins and lipids associated with nucleic acids into an organic phase. However, phenol-based reagents must later be carefully removed from any nucleic acid preparation because phenol is toxic and interferes with downstream processes (such as sequencing or hybridization) that may be used to analyze nucleic acid.

SUMMARY

In a first embodiment, the invention provides a method for binding a nucleic acid molecule to a substrate in the presence of phenol. For example, the method can comprise (a) obtaining sample comprising a nucleic acid molecule and phenol and (b) contacting the sample to a silica substrate in the presence of a binding agent comprising a chaotropic salt, an alcohol or a combination thereof, thereby binding the nucleic acid molecule to the silica substrate. In certain aspects, a nucleic acid containing sample may comprise a substantial amount of phenol, such as about or greater than about 10%, 20%, 30%, 40% or 50% phenol by volume.

In a further embodiment, the invention provides a method for nucleic acid purification comprising (a) contacting a nucleic acid containing sample with a denaturing solvent comprising phenol; (b) adding a binding agent to the sample, wherein the binding agent comprises a chaotropic salt, an alcohol or a combination thereof; and (c) contacting the sample with a silica substrate thereby binding the nucleic acid to the silica substrate. A nucleic acid purification method according to the invention may comprise performing steps (a)-(c) in any order. Alternatively or additionally, two or more of steps (a)-(c) may be performed essentially contemporaneously. For example, a binding agent and silica substrate can be added to a sample contemporaneously (e.g., as part of the same reagent) or a binding agent may be added to a sample prior to contacting the sample with a denaturing solvent comprising phenol. In still further aspects, steps (a) and (b) may be performed contemporaneously, for example, by contacting the sample with the denaturing solvent comprising phenol and the components of a binding agent.

In certain embodiments, the nucleic acid in a sample comprising phenol are substantially unprecipitated prior to binding of the nucleic acid to the silica substrate. For example, in certain aspects, prior to binding of the nucleic acid to the substrate, at least about 90% of the nucleic acid remains in solution in the sample. In certain instances, a sample comprising phenol may comprise an aqueous and an organic phase. Thus, in one aspect of the invention, the nucleic acid is bound to the silica substrate with out substantially separating the organic and aqueous phases in the sample (e.g., without removing a substantial portion of one phase or the other from the sample prior to the binding). Thus, in some aspects, a method of the invention may be defined as a method for directly binding a nucleic acid molecule to silica substrate from an aqueous/organic suspension. In further aspects, a method according to the invention does not comprise a centrifugation step (such as a step to form a nucleic acid pellet by centrifugation) prior to the binding of the nucleic acid to the silica substrate. Thus, in certain aspects, a method according to the invention may be defined as a method for binding at least about 50%, 60%, 70%, 80%, 90%, 95% or more of the nucleic acid (e.g., RNA and/or DNA) from a sample to a silica substrate.

In certain embodiments, methods of the invention involve denaturing solvents comprising phenol (or carbolic acid). For example, in certain aspects, a denaturing solvent comprises greater than about 30% phenol by volume, such as at least about 40%-60% phenol. In some aspects, such denaturing solvents are acidic, having a pH of less than about 6.0, 5.5, 5.0, or 4.5 (e.g., a pH of about 4.0). In certain aspects a denaturing solvent has a pH of between about 6.0, 5.5, 5.0, 4.5, 4.0 and about 3.5, 3.0, 2.5 or 2.0. Thus, in some cases, denaturing solvents comprising phenol are equilibrated with an aqueous buffer to a desired acidic pH, such as a pH of less than 5.0 (e.g., between about 5.0 and about 3.0). Denaturing solvents may further comprise additional ingredients including, but not limited to, chloroform, isoamyl alcohol, guanidinium thiocyanate, guanidinium chloride, BCP (1-bromo-3-chloropropane) BAN (4-bromoanisole), an antioxidant (e.g., 2-mercaptoethanol), a chelating agent (e.g., EDTA or EGTA) or isoamyl alcohol. For example, an agent may comprise phenol, guanidinium thiocyanate and other components at a ratio of about 5:3:2. For example, a denaturing solvent can be selected from one of those provided in U.S. Pat. No. 4,843,155, incorporated herein by reference in its entirety. Commercially available denaturing solvents that may be used according the invention include, but are not limited to, TRI Reagent®, RNAzol® (Molecular Research Center), TRIzol® (available from Invitrogen) and Qiazol® (available from Qiagen).

Some aspects of the invention concerns the addition of at least a first binding agent to a sample to facilitate nucleic acid binding to a silica substrate. For example, the binding agent may comprise an alcohol such as a lower alcohol, e.g., methanol, ethanol, isopropanol, butanol, 1-methyl-3-butanol or a combination thereof. In some embodiments the binding agent can comprise Dioxane which is used similarly to or substituting for alcohols including lower alcohols (e.g., 1,4-Dioxane or rare 1,2 or 1,3 isomers of Dioxane). In some embodiments, the binding agent is a substantially aqueous solution comprising a chaotropic salt. For example, the binding agent may be an aqueous solution comprising a buffering agent, an alcohol, a chaotropic salt, a chelating agent and/or a detergent. A binding agent can be added to a sample comprising nucleic acid before, after or contemporaneously with the contacting of the sample to a silica substrate. Thus, in some aspects, a binding agent may further comprise a silica substrate, such as a slurry of silica beads.

In certain embodiments, the binding agent may be a substantially aqueous solution comprising one or more chaotropic salts and, optionally, an alcohol. For example, a binding agent may comprise a chaotropic salt (e.g., guanidinium thiocyanate, guanidinium hydrochloride sodium iodide, sodium perchlorate, urea or thiourea) or a mixture of chaotropic salts and an acetate salt (e.g., sodium acetate) and may, or may not, comprise an alcohol. In certain aspects, a binding agent comprises a concentration of an acetate salt such that, after addition of the binding agent, the sample comprises a concentration at least about 100 mM (e.g., about 0.1 M to 1.0 M) relative to the acetate salt. Alternatively or additionally, a substantially aqueous binding agent comprises an alcohol such that the total alcohol content of the sample after the binding agent is added is about 2.5% to about 40% alcohol. In some aspects, a substantially aqueous binding agent comprises at least or at most about 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0 percent alcohol or any range derivable therein. For example, the binding agent can comprise about 20%-40%, about 20%-30% alcohol, about 2.5%-25%, about 2.5%-20% alcohol or about 5%-25% alcohol. Such aqueous binding agents may be used, for example, to bind DNA molecules to a silica substrate. In still other embodiments the binding agents can comprise Dioxane such that the total Dioxane content of the sample after the binding agent is added is about 2.5% to about 30% Dioxane (e.g., about 2.5%-25%, about 2.5%-20% Dioxane or about 5%-25% Dioxane). In yet further aspects, a substantially aqueous binding agent comprises about 20%-30% or about 20%-40% Dioxane or about 40%-100% Dioxane. Such aqueous binding agents may be used, for example, to bind DNA molecules to a silica substrate.

In further embodiments, the binding agent may be a substantially alcohol binding agent such as an agent that increases the total alcohol content of the sample to greater than about 40% after addition (e.g., an agent that increases the total alcohol content of the sample to greater than about 45%, 50%, 55% or 60%). For instance, a substantially alcohol binding agent may be a solution that is 80%, 90%, 95%, 98% or essentially 100% alcohol, such as a lower alcohol (e.g., ethanol). Such alcohol-based binding agents may be used, for example, to bind RNA or RNA and DNA molecules to a silica substrate. In certain aspects, the binding agent may further comprise a phase separating agent.

In a further embodiment, a method of the invention comprises one or more steps selected from the group consisting of: adding a phase separating agent to a sample; removing the sample suspension from the silica substrate after binding of the nucleic acid; contacting a silica substrate bound nucleic acid with a wash agent (e.g., washing the silica substrate); and eluting the nucleic acid from the silica substrate with an elution buffer. For example, a phase separating agent, such as an agent comprising chloroform, BCP (1-bromo-3-chloropropane) or BAN (4-bromoanisole) can be added. Wash agents for use according to the invention may, for example, comprise an aqueous solution with high salt and/or alcohol content and optionally may include detergents. Examples of elution buffers include, but are not limited to, aqueous solutions such as solutions comprising a buffering agent, a chelating agent and/or one or more nuclease inhibitors.

Methods according to the invention may be used for the purification of DNA (e.g., genomic or plasmid DNA), RNA or a combination thereof. In certain embodiments, a method of the invention is used for the isolation of RNA and the binding agent comprises a substantially alcohol binding agent. In another embodiment, a method according to the invention is used for DNA purification and the binding agent comprises a substantially aqueous buffer (e.g., an aqueous buffer comprising a chaotropic salt, an alcohol and, optionally, a detergent).

In still a further embodiment, a method according to the invention may be used to sequentially purify DNA and RNA. For instance, an aqueous binding agent comprising a chaotropic salt may be added to a sample comprising a nucleic acid and the suspension contacted with a first silica substrate to bind DNA from the suspension. In one example, an aqueous binding agent for DNA binding additionally comprises an alcohol and can be used to raise the alcohol content of the suspension to about 5-20%. In a second example, an aqueous binding agent for DNA binding additionally comprises an acetate salt and can be used to raise the acetate content of the sample to about or above about 0.1 M, 0.2 M, 0.3 M, 0.5 M, 0.75 M, or 1.0 M. Following removal or collection of the silica-bound DNA, the suspension can then be mixed with a second binding agent, such as a substantially alcohol binding agent and contacted with a second silica substrate to bind RNA from the suspension. For example, the second binding agent for RNA binding can be used to raise the alcohol content of the suspension to greater than about 50%. DNA and RNA may then be eluted from the first and second silica substrates accordingly. Thus, methods for preferentially purifying DNA and RNA from the same sample suspension are also provided by the instant invention.

In certain aspects, methods according to the invention concern a silica substrate. A variety of silica substrates may be used according to the invention including, but not limited to, silica beads (e.g., magnetic beads), fibers, silica plates or a porous silica matrix. In certain aspects, a silica substrate is immobilized such that a suspension or a solution can be moved over or through the substrate. For example, a silica substrate may be comprised in a column or in an array of columns (see, e.g., U.S. Patent Publication 20100222560, incorporated herein by reference). In certain aspects, a column for use according to the invention is adapted such that suspensions or solutions can be pushed (e.g., by applying pressure via a pipette) or pulled (e.g., by a vacuum pressure) through a column. Thus, in certain aspects, a method for nucleic acid purification according to the instant invention does not comprise a step involving centrifugation. A variety of materials may be used to manufacture a column for use according to the methods of the invention. In certain aspects, the column or the interior surfaces thereof are composed of a material that is substantially resistant to degradation by phenol (e.g., polypropylene). In still further aspects, a column for use according to embodiments is comprised in an array of columns such as in an array of 96 or 384 columns (e.g., adapted for use with a corresponding 96- or 384-well microtiter plate).

A sample for use according to the invention may be any sample that comprises or potentially comprises a nucleic acid. For example, the sample may comprise genomic DNA, plasmid DNA or RNA. For instance the sample may comprise RNA, such as mRNA or rRNA or small RNA molecules. As used herein a small RNA molecule refers to a molecule less than about 200 nucleotides (e.g., less than about 150, 100 or 50 nucleotides) in length. Examples of such molecules include, without limitation, small interfering RNAs (siRNAs), micro RNAs (miRNAs), piwi RNAs (piRNAs), as well as small synthetic RNAs, such as RNA oligonucleotides. In further aspects, a sample of the embodiments is a sample that is substantially free of larger RNAs (RNAs over 200 nucleotides in length) and/or free of DNA. In some aspects, a method of the embodiments is further defined as method for isolating or purifying a small RNA.

A sample can be obtained from a variety of sources such as from an animal subject, a plant or from a cell line or tissue bank. A sample may be a fresh sample or a frozen or desiccated sample. For example a sample from an animal may be a blood sample (e.g., a whole blood sample), a urine sample, a fecal sample, a tissue sample (e.g., a biopsy), a saliva sample, or a hair sample.

In certain embodiments, methods according to the invention may further comprise one or more treatment steps prior to binding of nucleic acid to a silica substrate. In certain aspects, a sample, such as a tissue sample, can be disrupted prior to treatment with denaturing solvent. A sample can, for example, be disrupted mechanically by chopping or grinding or enzymatically (e.g., by proteinase digestion). In some aspects, a method involves a step for shearing genomic DNA in the sample prior to binding of nucleic acid to a silica substrate. For example, the shearing can be mechanical shearing (e.g., repeated pipetting or sonication) or limited enzymatic digestion.

In still a further embodiment, a method according to the invention may be defined as a method for purifying nucleic acid from a plurality samples. For example, nucleic acid may be purified from at least 2, 5, 10, 15, 20, 25, 50, 100, 200 or 1000 samples. In still a further embodiment, a method for the invention is automated. For instance, one, two or more steps of a method according to the invention can be performed by a robot or a microfluidic device.

In a further embodiment a method is provided for purifying nucleic acid molecules from whole blood or from blood cells, comprising (a) contacting sample comprising whole blood or blood cells with a denaturing solvent comprising phenol; (b) adding a binding agent to the sample, wherein the binding agent comprises a chaotropic salt, an alcohol or a combination thereof; and (c) contacting the sample with a silica substrate thereby binding the nucleic acid to the silica substrate, wherein the sample comprises an aqueous and an organic phase after the addition of the denaturing solvent and wherein the aqueous and organic phases are not separated prior to binding the nucleic acid to the silica substrate. In some aspects, a method further comprises sedimenting (e.g., by centrifugation) the sample and denaturing solvent to remove excess cell debris.

In still a further embodiment an automated method is provided for purifying nucleic acid molecules from a sample, comprising (a) contacting a nucleic acid sample with a denaturing solvent comprising phenol; (b) adding a binding agent to the sample, wherein the binding agent comprises a chaotropic salt, an alcohol or a combination thereof; and (c) contacting the sample with a silica bead (e.g., a magnetic bead) thereby binding the nucleic acid to the bead, wherein the sample comprises an aqueous and an organic phase after the addition of the denaturing solvent and wherein the aqueous and organic phases are not separated prior to binding the nucleic acid to the bead. In further aspects, steps (a), (b) and/or (c) are performed by a robot. In a related aspects, a computer-readable medium is provided comprising a program for instructing a robot to perform steps (a), (b) and/or (c) of a method of the embodiments.

In yet a further embodiment a method is provided for selectively purifying small RNA molecules, comprising (a) contacting a nucleic acid containing sample with a denaturing solvent comprising phenol; (b) adding a binding agent to the sample, wherein the binding agent comprises a chaotropic salt, an alcohol or a combination thereof; (c) contacting the sample with a silica substrate thereby binding the nucleic acid to the silica substrate; and (d) selectively eluting small RNA molecules from the silica substrate with an elution buffer (e.g., a buffer comprising at least one chaotropic agent and at least one alcohol). In some aspects, the method further comprises (e) binding the eluted small RNA molecules to a second silica substrate in the presence of a further binding buffer; and, optionally, (f) eluting the small RNA molecules from the second silica substrate. Thus, in some aspects, a methods of the embodiments comprise selectively purifying or isolating small RNA molecules such as miRNAs, siRNAs, piRNAs and/or synthetic RNAs.

In still a further embodiment, the invention provides kits for purification of nucleic acid. In one aspect, a kit may comprise: a denaturing solvent comprising phenol; at least a first binding agent; and a silica substrate (e.g., magnetic beads). In certain aspects, a kit comprises instructions for binding nucleic acid to a silica substrate without one or more of the following steps prior to the binding: (i) precipitating nucleic acid; (ii) separating the organic and aqueous phases of a suspension or (iii) centrifugation of the sample or suspension. In still further embodiments, a kit according to the invention comprises a substantially aqueous binding agent and/or a substantially alcohol binding agent. Additional compositions that may be comprised in a kit of the invention include, but are not limited to, columns; one or more further organic solvents; one or more wash agent; one or more elution buffer; a phase separating agent (e.g., chloroform); DNase enzymes, one or more detergent, one or more column (e.g., a set of columns arrayed in a 96-well format), a proteinase; a reference sample and/or storage tubes. In certain aspects, components of a kit of the invention may be nuclease-free.

In a further embodiment, there is provided a reagent comprising (i) a denaturing solvent (e.g., a solvent comprising phenol); (ii) a binding agent (e.g., comprising a chaotropic salt, an alcohol or a mixture thereof); and (iii) a silica substrate. For example, a reagent of the embodiments can comprise a mixture of a denaturing solvent and a binding agent and a suspension of silica beads. Such a regent can, in some aspects, be packaged in a bottle, a vial or column. Kits comprising a reagent of the embodiments are also provided.

As used herein, "a" or "an" may mean one or more. As used herein in the claim(s), when used in conjunction with the word "comprising", the words "a" or "an" may mean one or more than one.

The use of the term "or" in the claims means "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

The following drawings are part of the present specification and are included to further demonstrate certain aspects of the present invention. The invention may be better understood by reference to the drawings in combination with the detailed description of specific embodiments presented herein.

DETAILED DESCRIPTION

Figure 1:
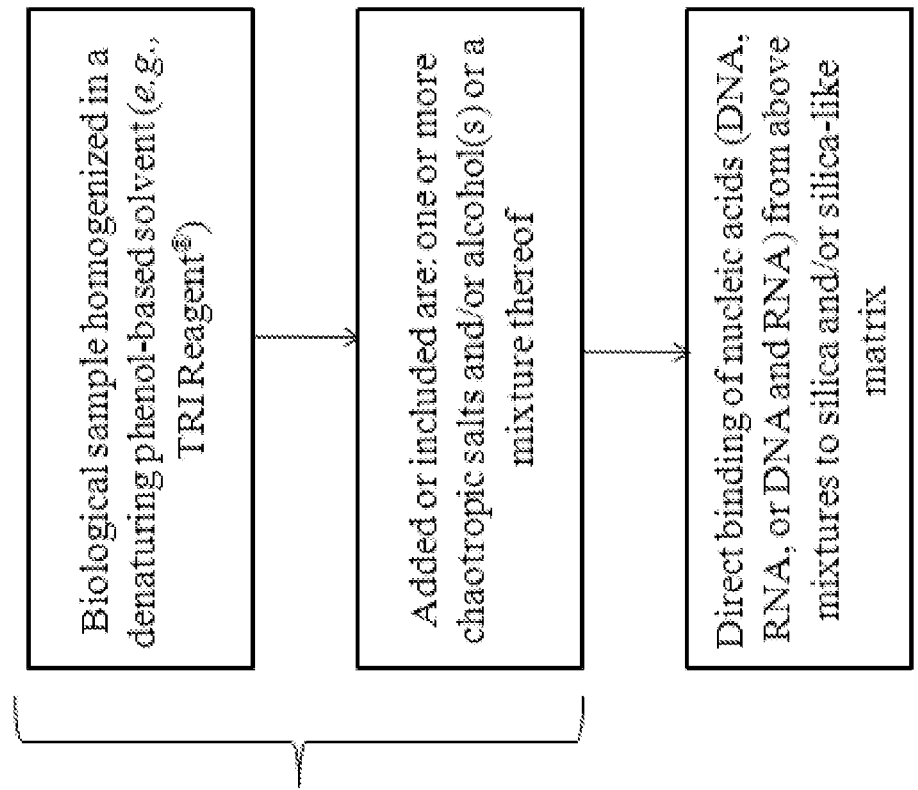
FIG. 1: A non-limiting exemplary protocol for isolation of nucleic acid according to the invention.

The instant invention provides an efficient method for nucleic acid isolation from samples. In particular, methods of the invention allow the binding of nucleic acids directly from an organic sample suspension to a silica substrate. For example, by adding an aqueous binding buffer to an organic suspension DNA can be efficiently bound to a silica matrix and purified away from contaminating protein and cell debris. Likewise, an alcohol based binding buffer can be used to directly bind RNA (and DNA) to silica from an organic suspension. Thus, the methods of the instant invention can be used to purify RNA (including small RNA molecules such as siRNA and miRNA), DNA, DNA and RNA or to preferentially purify RNA and/or DNA The direct binding of nucleic acids from an organic suspension offers a number of advantages relative to other protocols for purification. First, the organic and aqueous phases of a suspension do not need to be separated, which is time consuming and typically involves centrifugation of the suspension and laborious removal of the aqueous (or organic) phase. Moreover, because any residual phenol contamination can inhibit the effectiveness of downstream sample treatments (e.g., nucleic acid sequencing), one or more additional step involving extracting the sample with a further organic compound is often required to reduce phenol contamination. Second, there is no need to precipitate nucleic acid out of solution. Again, this process is labor intensive and, in the case of samples containing small amounts of nucleic acid, can result in almost complete loss of the sample's nucleic acid. The direct binding of nucleic acids also has the advantage of reducing the opportunity for nuclease attack of the nucleic acids from the sample. In particular, because the methods of the invention do not involve additional precipitation and centrifugation steps in aqueous buffers the period over which the nucleic acids could be exposed to any active contaminating nuclease is reduced. Likewise, because the sample does not need to be transferred to multiple containers the chance of importing exogenous nuclease is reduced. The foregoing advantages of the new purification methods make them ideal for modern high throughput protocols which require reduced labor input.

I. GENERAL PROTOCOL

An illustrative and non-limiting protocol for nucleic acid purification according to the invention is exemplified below.

A. Sample Extraction

Samples may be processed for example, by freeze-thaw, proteinase treatment or mechanical homogenization prior to organic extraction. Organic extraction may be accomplished with a protein denaturing reagent such as a phenol composition or acidic phenol (carbolic acid) composition with guanidinium thiocyanate, to form a suspension. Protein denaturing reagents may additionally comprise components such as a phase separating agent (e.g., chloroform), an antioxidant (e.g., 2-mercaptoethanol or lipoic acid) or a chelating agent. An example composition can comprise phenol:guanidinium thiocyanate:other component(s) (at a ratio of 5:3:2). Once the denaturing solvent is added, the sample may be further homogenized, for example, by vigorous shaking or blending to solubilize all possible cell components. An organic and aqueous phase may form in a sample which comprises phenol, but such phase separation is not required for purification.

B. Addition of Binding Agent

A binding agent is added to the sample. In particular the binding agent comprises a chaotropic salt, an alcohol, Dioxane or a mixture thereof that facilitates nucleic acid binding to a silica substrate.

In the case of DNA, the binding agent is a substantially aqueous agent with chaotropic salt(s). A binding agent may also comprise additional buffer agents, salts, detergents and/or alcohol (e.g., lower alcohols such as ethanol or isopropanol). For example, the binding agent may comprise 4-5 M guanidinium thiocyanate (GTC), 5-20% isopropanol, 2-10% glycerol and detergents. In another example, the binding agent comprises 4-5 M GTC, 0.1-1.0 M sodium acetate and, optionally, detergents. One to six volumes of the binding agent are typically added to one volume of a phenol containing sample (e.g., 1:1, 1:2, 1:3, 1:4, 1:5 or 1:6 volumes of binding agent:sample+phenol).

In the case of RNA (or RNA/DNA), the binding agent is a substantially alcohol agent, such as ethanol or isopropanol. After addition of a substantially alcohol agent the total concentration of alcohol in the sample is typically raised to greater than about 20%. For embodiments where binding of both DNA and RNA is desired a binding buffer may comprise both a chaotropic salt, such as GTC, and an alcohol.

C. Nucleic Acid Binding to Silica

The sample comprising the binding agent is then contacted to a silica substrate. If an aqueous phase has formed in the sample then the aqueous phase alone may be contacted with the silica substrate. However, separation of organic and aqueous phases is not required for binding. The term "silica" as used herein refers materials comprising a build-up of silicon and oxygen. Such materials include, without limitation, silica, silicon dioxide, silica gel, fumed silica gel, diatomaceous earth, celite, talc, quartz, glass, glass particles including all different shapes of these materials. Particles, for example, may comprise particles of crystalline silica, soda-lime glasses, borosilicate glasses, and fibrous, nonwoven glass. In certain aspects, a silica bead may be a magnetic silica bead (see, e.g., PCT Patent Publn. WO 98/31840, incorporated herein by reference).

Following binding of the nucleic acid the remaining sample suspension is removed by, for example, pipette, vacuum or centrifugation.

D. Optional Addition of a Second Binding Agent

In certain cases, DNA can be bound to silica, while the majority of RNA remains unbound in the sample. In this case, the remaining sample can be collected and a second binding agent added. The binding agent can be a substantially alcohol agent or Dioxane agent for binding RNA such that, after addition, the total concentration of alcohol in the sample is raised to greater than about 20%, such as to a concentration of about 50% or higher.

E. Optional Second Binding to Silica

The sample and binding agent are contacted with a second silica substrate (as above) to bind additional remaining nucleic acid, such as RNA, from the sample. The remaining sample suspension is then removed as in step 3. The remaining sample may be held for further analysis, such as protein or lipid analysis, or discarded.

F. Wash of Silica Substrate with Bound Nucleic Acid

The silica substrate (and/or second silica substrate) comprising bound nucleic acid is washed one or more times with a washing agent. Washing agents may comprise, for example, solutions comprising alcohol, salts, buffering agents and/or detergents, that do not elute substantial amounts of nucleic acid from the silica. For example, a wash buffer may comprise about or greater than about 40%, 50%, 60%, 70%, 80% or 90% alcohol. In certain aspects the alcohol is a volatile alcohol, such as ethanol. Example washing agents include, but are not limited to, a solution of 20%-50% ethanol and 20%-50% isopropanol; a solution of about 0.1-4.0 M guanidinium hydrochloride, detergents and up to about 80% ethanol; or a solution of about 80% ethanol.

G. Elute Nucleic Acid from the Silica Substrate

The silica substrate (and/or second silica substrate) comprising bound nucleic acids is contacted with an elution buffer to remove the bound nucleic acid into solution. Elution buffers typically comprise a pH buffer agent, limited levels of salts and/or chelating agents. Buffer may additionally comprise nuclease inhibitors.

Following elution nucleic acids may either be further purified or used directly in down-stream analysis such as hybridization or sequencing.

II. REAGENTS AND KITS

Kits may comprise suitably aliquoted reagents of the present invention, such as an acid-phenol denaturing solvent, one or more binding agent and a silica substrate. Additional components that may be included in a kit according to the invention include, but are not limited to, one or more wash buffer including a magnetic bead (i.e., magnetic silica beads such as MagBinding Beads) Pre-wash buffer, an elution buffer, a proteinase composition, DNase and/or RNase inhibitors, DNase or RNase enzymes, oligonucleotide primers, reference samples (e.g., samples comprising known amounts of DNA or RNA), distilled water, DEPC-treated water, probes, sample vials, polymerase, magnetic binding beads (e.g., magnetic silica beads such as MagBinding Beads), 96-well silica plates, 96-well collection plates, cover foils for 96 well plates and instructions for nucleic acid purification. In certain further aspects, additional reagents for DNA and/or RNA clean-up may be included.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing reagent containers in close confinement for commercial sale. Such containers may include cardboard containers or injection or blow-molded plastic containers into which the desired vials are retained.

When the components of the kit are provided in one or more liquid solutions, the liquid solution is an aqueous solution, with a sterile aqueous solution being preferred. However, the components of the kit may be provided as dried powder(s). When reagents and/or components are provided as a dry powder, the powder can be reconstituted by the addition of a suitable solvent. It is envisioned that the solvent may also be provided in another container means.

III. EXAMPLES

The following examples are included to demonstrate certain embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1: RNA Isolation from Human Cells

Various techniques were used for purification of RNA from human cells that were frozen at −80° C. RNA was isolated from ~100,000 frozen human cells resuspended in 50 μl of water. Samples in lanes 2-6 were lysed in 125 μl of RNAzol® and further were added one or more of the following, water, ethanol, isopropanol (indicated as "Treatment" in the Table 1). Samples in lanes 7-10 were lysed in 200 μl TRIreagent® and further were added one or more of the following, chloroform, ethanol, isopropanol (indicated as "Treatment" in the Table 1.). Samples in lanes 2-5 and 7-9 were processed by column purification using a silica matrix. Each suspension mixture including all components as indicated in "Treatment" (Table 1) was loaded onto the Zymo-Spin™ IC column (Zymo Research, Irvine Calif.), centrifuged at 12,000×g, and flow-through discarded. The column was washed once with 700 μl RNA Wash Buffer then centrifuged in an empty collection tube to remove residual ethanol. RNA was eluted from the column with 15 μl water. Samples 6 and 10 are controls and were processed according to manufacturer's instructions, i.e., to separate aqueous and organic phase, samples were centrifuged. The aqueous phase was then precipitated with isopropanol, RNA pellet washed twice with 70% ethanol, then resuspended in 15 μl water. Sample in lane 11 was lysed in 150 μl of ZR RNA Buffer and processed according to the protocol for Quick-RNA™ MicroPrep (Catalog number R1050, Zymo Research, Irvine Calif.).

Figure 2:
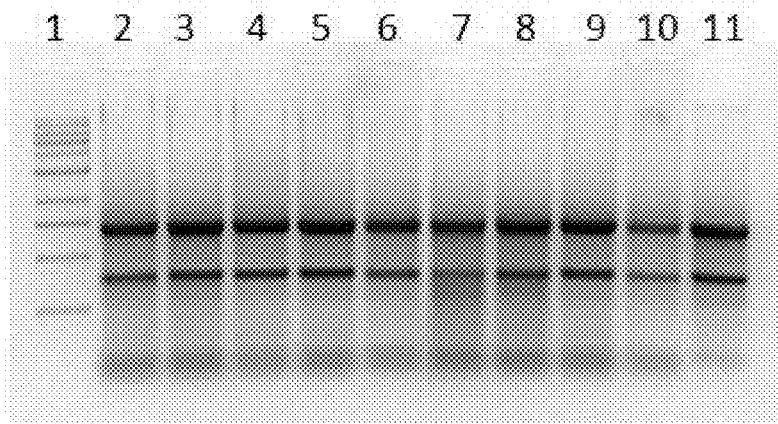
FIG. 2: Visualization of RNA isolated in the studies of Example 1 following electrophoresis on a 1% agarose gel. Treatment conditions for the samples loaded in lanes 1-11 (from left to right) are as follows (1) 1 KB ladder; (2) RNAzol®+H$_2$O+isopropanol; (3) RNAzol®+isopropanol; (4) RNAzol®+H$_2$O+ethanol; (5) RNAzol®+ethanol; (6) RNAzol®-control; (7) TRIreagent®+isopropanol; (8) TRIreagent®+chloroform+ethanol; (9) TRIreagent®+ethanol; (10) TRIreagent®-control; (11) Quick-RNA™-control, see also Table 1.

Any RNA eluted after the indicated treatments was resolved by electrophoresis on a 1% agarose gel. Results from this study are shown in FIG. 2. Specifically, the results demonstrate that by using a binding agent comprising alcohol (such as ethanol or isopropanol) RNA could be efficiently bound to (and later eluted from) a silica matrix directly from the RNAzol® or TRIreagent® suspension (i.e., without the need for nucleic acid precipitation).

TABLE 1

Sample treatments for RNA shown in FIG. 2

| Lane | Label | Treatment |
| --- | --- | --- |
| 1 | 1kb | 1kb DNA marker |
| 2 | RNAzol ® + H₂O + isopropanol | +water (70 μl) + isopropanol (245 μl) |
| 3 | RNAzol ® + isopropanol | +isopropanol (175 μl) |
| 4 | RNAzol ® + H₂O + ethanol | +water (70 μl) + 95% ethanol (245 μl) |
| 5 | RNAzol ® + ethanol | +95% ethanol (175 μl) |
| 6 | RNAzol ®/control | +water (70 μl) |
| 7 | TRIreagent ® + isopropanol | +isopropanol (250 μl) |
| 8 | TRIreagent ® + chloroform + ethanol | +chloroform (50 μl) + 95% ethanol (300 μl) |
| 9 | TRIreagent ® + ethanol | +95% ethanol (250 μl) |
| 10 | TRIreagent ®/control | +chloroform (50 μl) + isopropanol (100 μl) |
| 11 | Quick-RNA ™-control | |

Example 2: DNA and RNA Isolation from Human Cells

Various techniques were used for purification of nucleic acid molecules from human cells that were frozen at −80° C. Frozen cell samples from ~50,000 human cells were resuspended in 25 μl of water. All samples (lanes 2-9 and 11) were lysed in 100 μl of TriReagent. Following the lysis, a binding agent was added to the sample as indicated under "Treatment" (Table 2). The mixtures including all components as indicated in "Treatment" (Table 2) were loaded onto the Zymo-Spin™ IC column (Zymo Research, Irvine Calif.), centrifuged at 12,000×g, and flow-through discarded (sample/lane 2-3, 5, 7-9, 11) or saved for further processing (sample/lane 4 and 6). 95% ethanol was added to the flow-through from samples/lanes 4 and 6 and the mixture was loaded onto the a new Zymo-Spin™ IC column, centrifuged at 12,000×g, and flow-through discarded. After binding, all columns were washed once with 700 μl RNA Wash Buffer then centrifuged in an empty collection tube to remove residual ethanol. RNA, DNA or DNA and RNA was eluted from the column with 15 μl water. Buffer used in the experiments are as follows: Buffer A (A; 4-5 M GTC, 5-20% isopropanol, 2-10% glycerol and detergents); Buffer B (B; 4-5 M GTC and 0.1 to 1.0 M sodium acetate); Buffer C (C; 4-5 M GTC, 0.1 to 1.0 M sodium acetate and detergents); and Buffer D (D; 1-5M GTC, 1-7M NaI, 20-60% ethanol and detergent).

Figure 3:
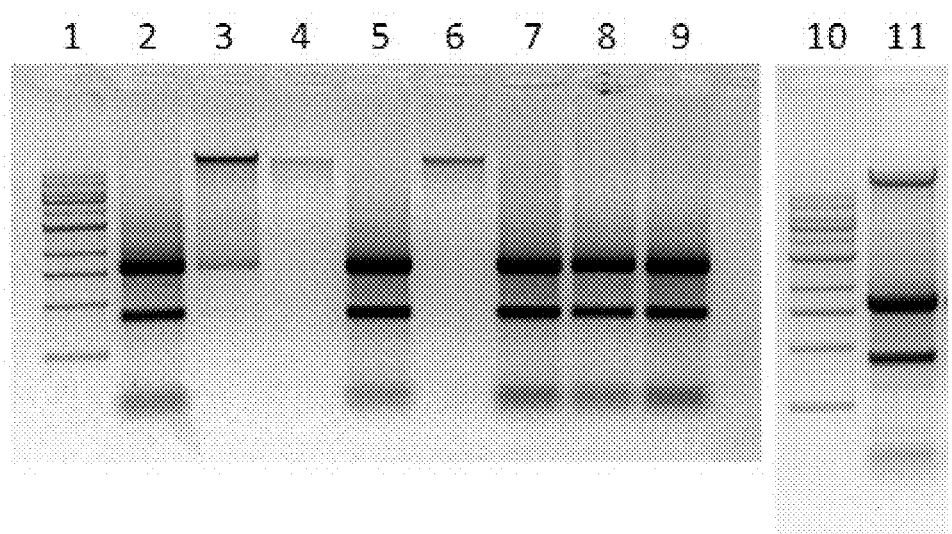
FIG. 3: Visualization of nucleic acid isolated in the studies of Example 2 following electrophoresis on a 1% agarose gel. Treatment conditions for the samples loaded in lanes 1-11 (from left to right) are as follows (1) 1 KB ladder; (2) buffer D; (3) buffer A; (4) buffer B; (5) column flow-through from lane 4 sample; (6) buffer C; (7) column flow-through from lane 6 sample; (8) ethanol; (9) isopropanol; (10) 1 KB ladder; (11) buffer C+ethanol, see also Table 2.

Any nucleic acid that was eluted from the column was resolved by electrophoresis on a 1% agarose gel. Results from this study are shown in FIG. 3 and demonstrate that both DNA and RNA could be directly bound to a silica matrix directly from the organic denaturing agent (such as TRIreagent®) suspension, without the need for nucleic acid precipitation. Furthermore, the results demonstrate that by using binding agents having different compositions DNA and RNA can be sequentially purified from sample. See, for example lanes 4 and 5 or 6 and 7 which show DNA and RNA isolated from the same sample, respectively.

TABLE 2

Sample treatments for results shown in FIG. 3

| Lane | Label | Treatment |
|---|---|---|
| 1 | 1 kb | 1 kb DNA marker |
| 2 | D | +Buffer D (375 µl) |
| 3 | A | +Buffer A (375 µl) |
| 4 | B | +Buffer B (375 µl) |
| 5 | B/FT | Sample/lane 4 column flow-through + 95% ethanol (500 µl) |
| 6 | C | +Buffer C (375 µl) |
| 7 | C/FT | Sample/lane 6 column flow-through + 95% ethanol (500 µl) |
| 8 | Ethanol | +95% ethanol (125 µl) |
| 9 | Isopropanol | +Isopropanol (125 µl) |
| 10 | 1 kb | 1 kb DNA marker |
| 11 | B + Ethanol | +Buffer B (250 µl) + 95% ethanol (375 µl) |

Example 3: Automated Nucleic Acid Isolation using Magnetic Beads

Isolation of RNA (DNA) from phenol-containing sample lysates, without phase separation, allows for direct binding of nucleic acids to a column matrix or beads, such as magnetic beads, and is ideal for automated sample processing. As an example of such automated processing samples were processed as detailed below the resulting RNA quantified and assess for quality.

1. $5 \times 10^5$ human epithelial cells were lysed in TRI Reagent and cleared by centrifugation.
2. Direct-zol™ Binding Buffer (see above) were added to the sample lysate (1:1 ratio) and mixed.
3. Magnetic silica beads (MagBinding Beads) were then added to the mixture to bind nucleic acids.
4. Beads are washed by 95-100% ethanol, Direct-zol™ MagBinding Bead PreWash, and 95-100% ethanol again, several times.
5. Optionally, during the wash steps, DNase I treatment can be performed with provided DNase I/10× Reaction Buffer.
6. Beads are dried and DNase/RNase-Free Water is added to elute RNA or DNA/RNA.

Figure 4A:
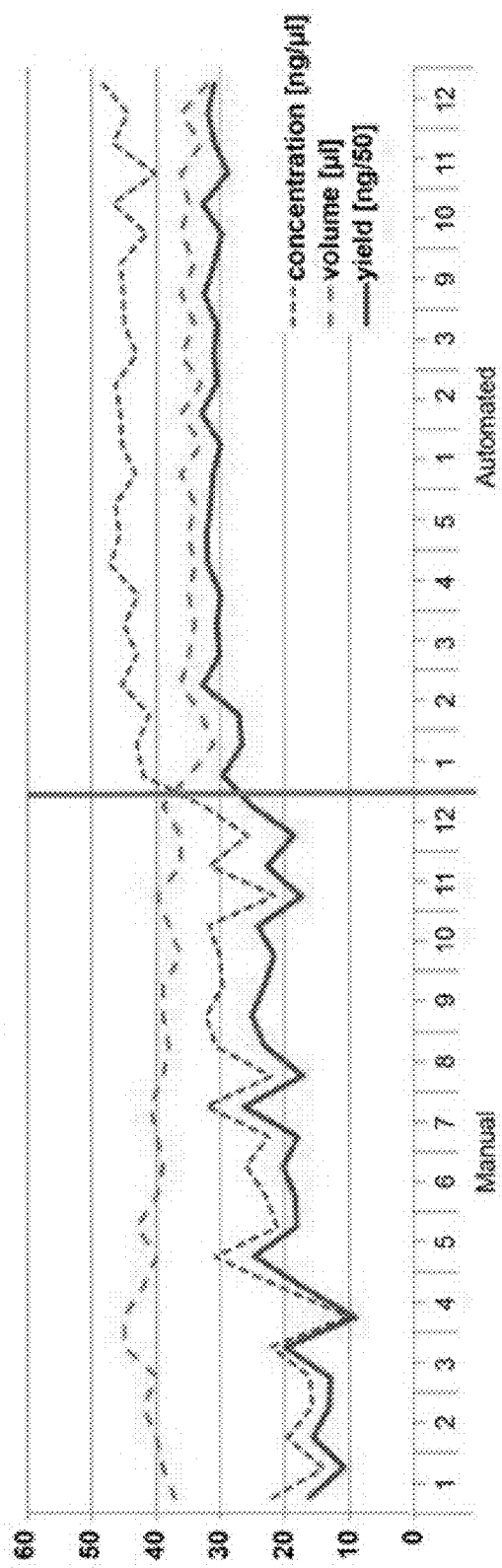
FIG. 4A-B: Reproducible automated sample processing. Isolation of RNA from phenol-containing sample lysates, without phase separation, allows for direct binding of nucleic acids to a column matrix or bead and for automated processing. A, Direct-zol™ MagBead RNA Isolation. Graph shows a comparison between manual and automated (Freedom EVO®, Tecan) sample processing by nucleic acid binding directly from a phenol-containing denaturing reagent using the Direct-zol™-96 MagBead RNA across a 96-well plate. In each case, RNA was purified from human epithelial cells (5×10$^5$/well). B, RNA was purified from human epithelial cells using the Direct-zol™-96 MagBead RNA on a Freedom EVO® automated system. RNA quality was assessed using a Bioanalyzer. RNA integrity number (RIN) demonstrates the high quality of the isolated RNA.
Figure 4B:
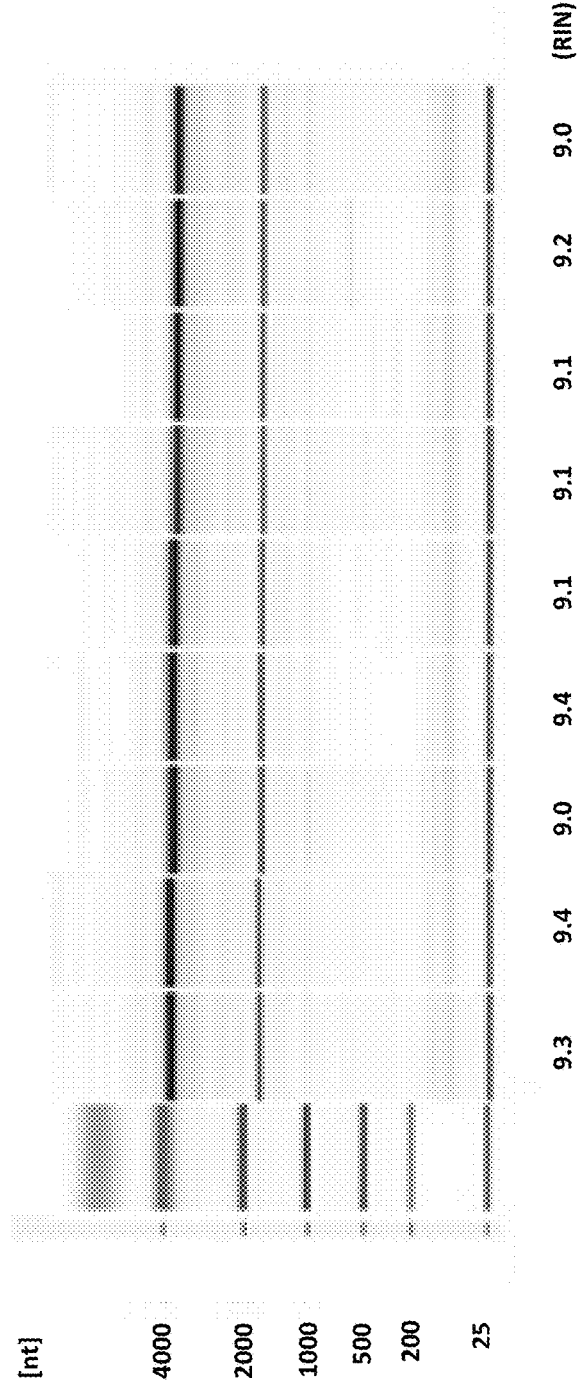

As shown in FIG. 4 methods of the embodiments proved highly effective in the context of automated sample processing. FIG. 4A demonstrates that reproducibly high concentration, high yield RNA can be obtained by automated sample processing according to the embodiments. Likewise, as shown in FIG. 4B the RNA obtained is of reproducibly high quality and shows little or no significant degradation.

Example 4: Small RNA Molecule Recovery

Experiments were undertaken to assess the efficiency of isolating small RNAs using methods of the embodiments. An example protocol for small RNA isolation is shown below:

1. RNA from human epithelial cells or mouse liver tissue homogenized in TRI Reagent was isolated by Direct-zol™ method and compared to the conventional phase separation. RNA was analyzed and quantified by a Small RNA Chip (Bionalyzer; FIG. 5).
2. A mixture of small RNA oligonucleotides (ZR small-RNA ladder) was recovered directly or "spiked" into a total RNA and recovered by the Direct-zol™ MagBinding Bead protocol. RNA was analyzed and quantified by a Small RNA Chip (Bioanalyzer; FIG. 5).

Figure 5A:
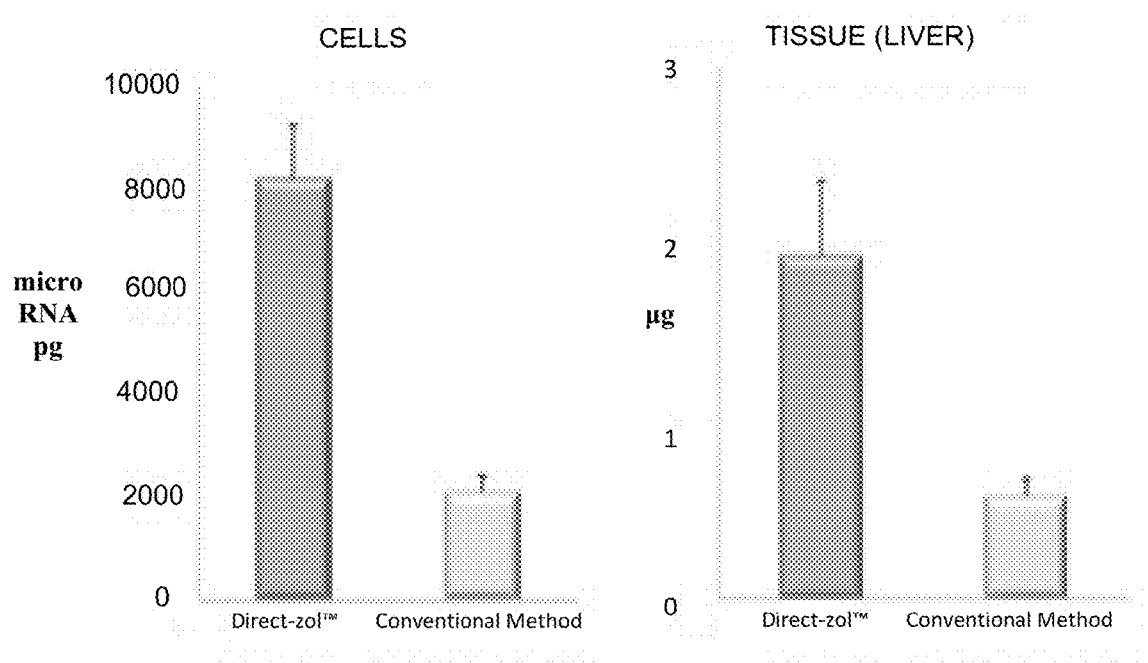
FIG. 5A-B: Isolation of small RNAs. Direct binding of RNA and small RNAs from phenol-containing lysates without phase separation, increases recovery of small RNAs compared to the conventional method (i.e., with phase separation/precipitation). A, Graph shows direct RNA isolation from phenolic extracts using a column capture, without phase separation (gray bars) versus a conventional phase separation method (lights bars). Methods of the embodiments show ~4× higher recovery of RNAs<40 nt as compared to a conventional phase separation method. B, Efficient small RNA isolation using a bead capture. Small RNA was recovered with the Direct-zol™-96 MagBead RNA system and gel-separated and imaged using a Bioanalyzer. Sample 1, indicates small RNA recovery from total RNA. Sample 2, indicates small RNA alone. Both samples were spiked with small-RNA ladder prior to Direct-zol™ MagBead purification.
Figure 5B:
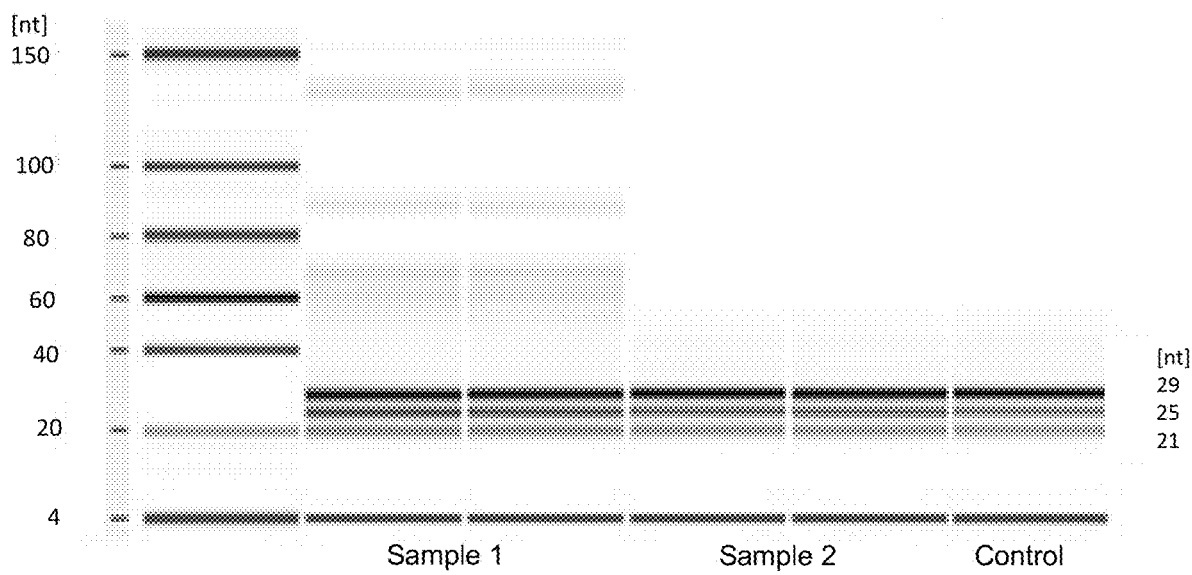

Results of the studies shown in FIG. 5A demonstrate that direct RNA isolation from phenolic extracts, without phase separation, shows higher recovery of RNAs<40 nt (4 fold higher) as compared to a conventional phase separation method. Again recovered RNA was shown to be of high quality (FIG. 5B).

Example 5: Nucleic Acid Extraction from Whole Blood

Both DNA and RNA can be isolated from phenol-containing whole-blood lysates directly, without phase separation. For these studies 100 ul of whole-blood (pig or human) was lysed in 300 ul TRI Reagent BD (TRI Reagent BD is for blood, plasma, serum) and cleared by centrifugation. The lysate/supernatant is aspirated and dispensed into a new tube. The lysate/supernatant can be processed either by spin-column/spin-plate (Direct-zol™ RNA MiniPrep, Direct-zol™-96 RNA) or magnetic silica bead format (Direct-zol™ MagBinding Bead RNA) as detailed below:

1. For spin-column/spin-plate: 95% ethanol is added to the lysate/supernatant (1:1 ratio) and the mixture is loaded into the column. Column is then washed by Direct-zol™ RNA PreWash and RNA Wash Buffer several times and RNA is eluted with DNase/RNase-Free Water.
2. For the silica magnetic bead format: Direct-zol™ Binding Buffer is added to the lysate/supernatant (1:1 ratio) and mixed. Magnetic silica beads (MagBinding Beads) are then added to the mixture to bind nucleic acids. Beads are washed by 95-100% ethanol, Direct-zol™ MagBead PreWash, and 95-100% ethanol again, several times. During the wash steps, DNase I treatment can be performed with provided DNase I/10× Reaction Buffer. Beads are dried and DNase/RNase-Free Water is added to elute the RNA or DNA/RNA.

Figure 6:
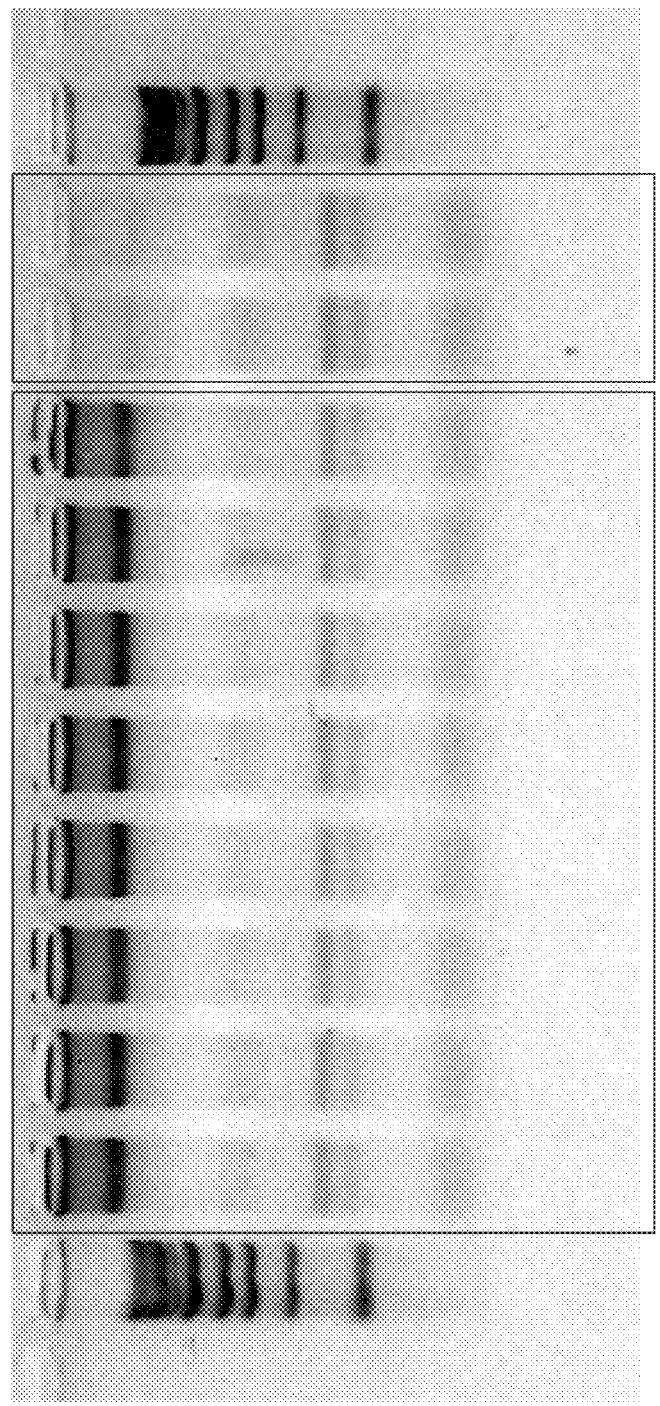
FIG. 6: Isolation of nucleic acid from blood samples. Both DNA and RNA can be efficiently isolated from phenol-containing whole-blood lysates directly, without phase separation. Gel shows nucleic acids efficiently isolated from whole blood in TRI Reagent without a phase separation. 100 µl whole blood (pig) was lysed in 300 µl TRI Reagent, cleared by centrifugation and nucleic acids bound to silica beads (Direct-zol™ MagBead system).

Results of the whole blood extraction are shown in FIG. 6 and demonstrate highly efficient isolation of RNA and DNA from the samples.

Example 6: Selective Isolation of Small RNAs

Studies were undertaken to determine if small RNA molecules could be selectively enriched using the methods of the embodiments. An example protocol for such selective enrichment is shown below:

1. Human epithelial cells were lysed in TRI Reagent and cleared by centrifugation.
2. 95% ethanol is then added to the sample lysate (1:1 ratio) and the mixture is loaded into the column.
3. small-RNA Elution Buffer, which comprises at least one chaotropic salt and at least one alcohol was added to the column. This removes/elutes small RNAs from the column (<200 nt).
4. To the flow-through that contains the small-RNAs (<200 nt), add 1 volume 95% ethanol and load the mixture into a new column.
5. Column is then washed by Direct-zol™ RNA PreWash and RNA Wash Buffer (see above) several times and RNA is eluted with DNase/RNase-Free Water.

Results of these studies demonstrate that small RNAs could be selectively purified relative to larger mRNA and rRNA components.

Figure 7:
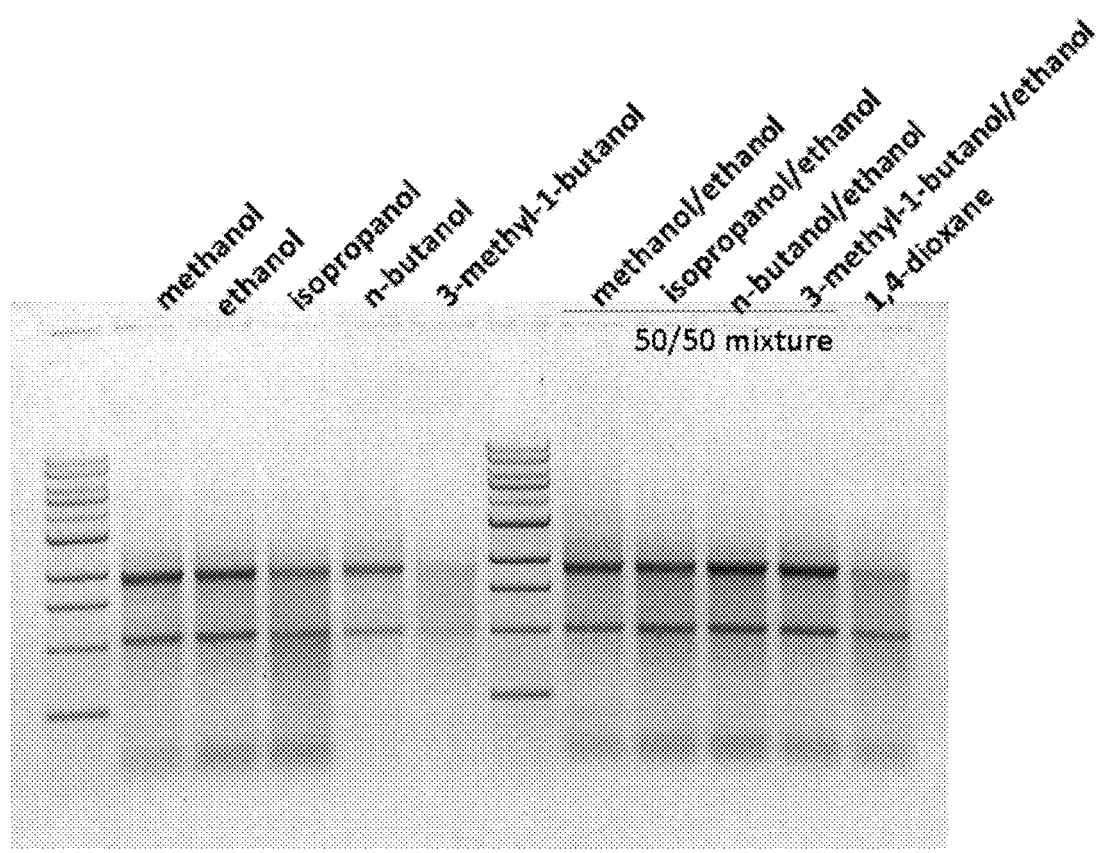
FIG. 7: Isolation of RNA from human cells is shown. High quality RNA is isolated from different binding buffers comprising different alcohols or mixtures of alcohols or Dioxane without phase separation.
Figure 8:
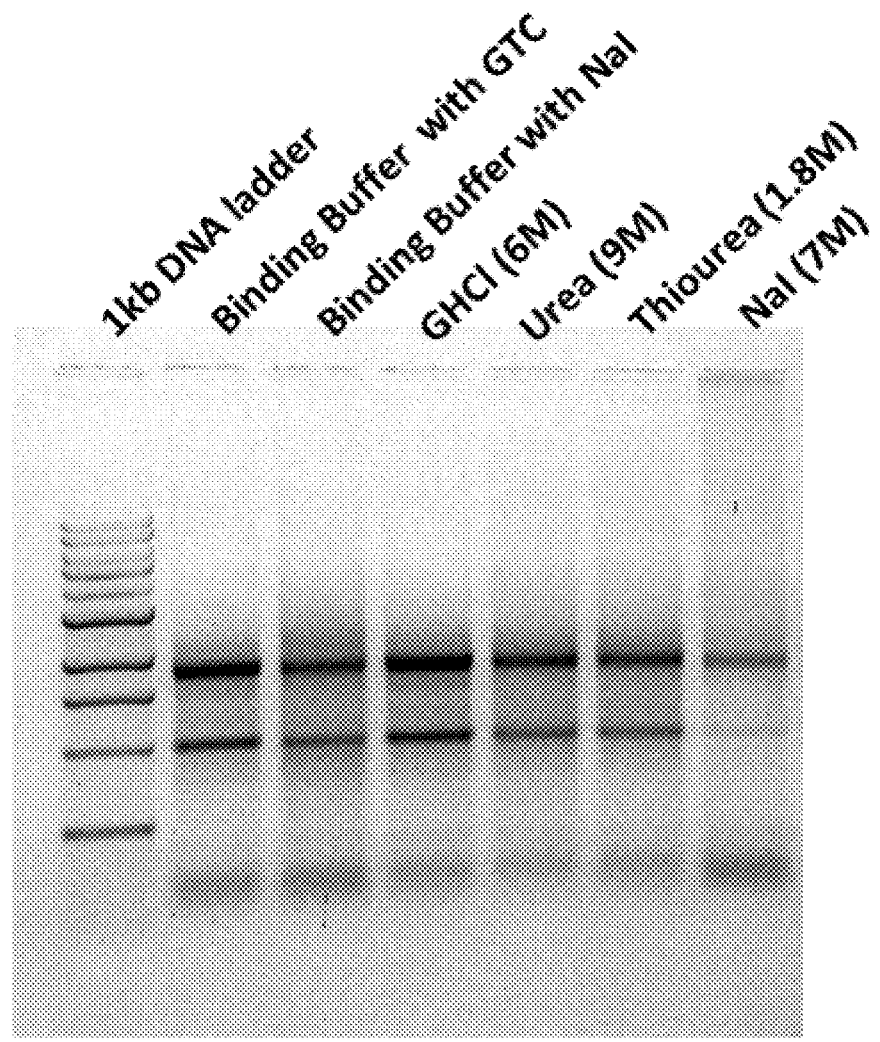
FIG. 8: Isolation of RNA from human cells is shown. High quality RNA is isolated from different binding buffers comprising different chaotropic salts.

Example 7: Isolation of RNA from Human Cells from Tri-Reagent with Different Binding Buffers RNA was isolated from about 50,000 human cells resuspended in 25 µl water. All samples were lysed in 100 ml TRI Reagent and further agents were added as follows:

(1) One volume (125 µl) of either 100% methanol, ethanol, isopropanol, n-butanol, 3-methyl-1-butanol or a mixture thereof (FIG. 7) or (2) one volume (125 µl) of a chaotropic salt or a buffer containing chaotropic salt, followed by two volumes (i.e. 250 µl) of 95% ethanol (FIG. 8).

Each mixture was loaded onto a separate spin Column (Zymo-Spin—IC, Zymo Research Corp.), centrifuged at 12,000×g with flow through being discarded after. Each column was then processed according to the protocol for the Direct-zol™ RNA miniprep, from step 3 on (Cat. No. 82050, Zymo Research Corp.). RNA was eluted with 15 µl DNAse/RNAse-free water. High-quality RNA is evident from all alcohols or Dioxane or chaotropic salts tested (FIG. 7 and FIG. 8, agarose gel electrophoresis and spectrophotometric analysis is shown below In Tables 3 and 4).

TABLE 3

Results for RNA binding with a variety of alcohol-based buffers

| Binding buffer component | ng/µl | 260/280 | 260/230 |
|---|---|---|---|
| methanol | 104.57 | 2.01 | 2.14 |
| ethanol | 130.51 | 2.02 | 2.19 |
| isopropanol | 132.02 | 2.02 | 2.26 |
| n-butanol | 75.48 | 2.04 | 2.21 |
| 3-methyl-1-butanol (IAA) | 53.13 | 1.98 | 2.00 |
| methanol/ethanol 50/50 | 108.99 | 2.01 | 2.12 |
| isopropanol/ethanol 50/50 | 133.24 | 2.03 | 2.26 |
| n-butanol/ethanol 50/50 | 136.75 | 2.03 | 2.23 |
| IAAl/ethanol 50/50 | 145.40 | 2.02 | 2.25 |
| 1,4-Dioxane | 126.07 | 2.02 | 2.2 |

TABLE 4

Results for RNA binding with a variety of chaotropic salts

| Binding buffer component | ng/µl | 260/280 | 260/230 |
|---|---|---|---|
| Binding buffer with GTC | 107.32 | 2.07 | 2.18 |
| Binding buffer with NaI | 112.04 | 2.05 | 1.28 |
| GHCl (6M) | 130.82 | 2.06 | 2.2 |
| Urea (9M) | 105.22 | 2.02 | 2.05 |
| Thiourea (1.8M)) | 106.44 | 2.05 | 1.81 |
| NaI (7M) | 87.17 | 2.02 | 2 |

REFERENCES

Each of the foregoing documents is hereby incorporated by reference in its entirety:
U.S. Pat. Nos. 4,843,155; 5,472,872; 6,210,945
U.S. Patent Publication 20100222560
PCT Patent Publn. WO 98/31840.
Sambrook et al., In: Molecular Cloning—A Laboratory Manual, 2001.

What is claimed is:

1. A method for binding a ribonucleic acid (RNA) to a silica substrate for purification comprising:
   (a) contacting a sample comprising whole blood or blood cells with a denaturing solvent comprising a guanidinium thiocyanate and at least 20% to 60% phenol, the denaturing solvent having a pH of 3.5-6.0;
   (b) adding a binding agent to the sample, wherein the binding agent comprises a chaotropic salt, a lower alcohol or a mixture thereof;
   (c) contacting the sample with a silica substrate, in the presence of at least 10% to 50% phenol, thereby binding the ribonucleic acid in the sample to the silica substrate;
   (d) washing the silica substrate and bound RNA with a wash solution; and
   (e) eluting the RNA from the silica substrate with an elution buffer, thereby providing purified RNA;
   wherein at least 90% of the RNA in the sample is unprecipitated prior to binding of the ribonucleic to the silica substrate, and wherein after the addition of the binding agent, the sample does not comprise separate aqueous and organic phases prior to binding the ribonucleic acid to the silica substrate.

2. The method of claim 1, wherein the denaturing solvent comprises at least one additional agent selected from the group consisting of a chaotropic salt, an antioxidant, a chelating agent, and a buffer.

3. The method of claim 1, wherein the method is automated.

4. The method of claim 1, wherein the binding agent is added to the sample before the denaturing solvent.

5. The method of claim 1, wherein the silica substrate is added to the sample before the binding agent.

6. The method of claim 1, wherein steps (a) and (b) are performed contemporaneously.

7. The method of claim 6, wherein steps (a), (b) and (c) are performed contemporaneously.

8. The method of claim 1, wherein the binding agent comprises a lower alcohol selected from the group consisting of methanol, ethanol, isopropanol, butanol, and a combination thereof.

9. The method of claim 1, wherein the total alcohol content of the sample is at least 40% after the binding agent is added.

10. The method of claim 1, wherein the binding agent is an aqueous solution comprising a chaotropic salt or mixture of chaotropic salts.

11. The method of claim 10, wherein the chaotropic salt is guanidinium thiocyanate, guanidinium chloride, sodium iodide, sodium perchlorate, urea or thiourea.

12. The method of claim 10, wherein the binding agent comprises pH buffer.

13. The method of claim 1, wherein steps (b) and (c) are performed contemporaneously.

14. The method of claim 1, wherein the ribonucleic acid is miRNA or siRNA.

15. The method of claim 1, wherein the silica substrate is in the form of beads, fibers or a porous matrix.

16. The method of claim 1, wherein the silica substrate is a (para)magnetic bead.

17. The method of claim 1, wherein the wash solution comprises a salt, a chaotropic salt, a detergent or an alcohol.

18. The method of claim 1, wherein in step (a) the guanidinium thiocyanate is present at a concentration of 0.5 M to 2 M.

* * * * *